(12) United States Patent
Rössling et al.

(10) Patent No.: US 6,207,135 B1
(45) Date of Patent: Mar. 27, 2001

(54) GASEOUS MICROPARTICLES FOR ULTRASONIC DIAGNOSIS AND PROCESS FOR THEIR PRODUCTION

(75) Inventors: Georg Rössling; Celal Albayrak; Matthias Rothe, all of Berlin (DE)

(73) Assignee: Inhale Therapeutic Systems, Inc., San Carlos, CA (US)

( * ) Notice: Subject to any disclaimer, the term of this patent is extended or adjusted under 35 U.S.C. 154(b) by 0 days.

(21) Appl. No.: 08/913,311
(22) PCT Filed: Mar. 14, 1996
(86) PCT No.: PCT/EP96/01108
    § 371 Date: Mar. 30, 1999
    § 102(e) Date: Mar. 30, 1999
(87) PCT Pub. No.: WO96/28192
    PCT Pub. Date: Sep. 19, 1996

(30) Foreign Application Priority Data
Mar. 14, 1995 (DE) .............................. 195 10 690

(51) Int. Cl.[7] ...................................... A61B 8/13
(52) U.S. Cl. ............................ 424/9.52; 424/9.5
(58) Field of Search ...................... 424/9.52, 9.5; 600/458

(56) References Cited

U.S. PATENT DOCUMENTS

| | | | |
|---|---|---|---|
| 4,718,433 | * | 1/1988 | Feinstein .................. 424/9.52 |
| 5,711,933 | * | 1/1998 | Bichon et al. .............. 424/9.52 |
| 5,820,850 | * | 10/1998 | Hashimoto et al. ........ 424/9.52 |
| 5,837,221 | * | 11/1998 | Bernstein et al. .......... 424/9.52 |
| 5,853,698 | * | 12/1998 | Straub et al. .............. 424/9.52 |
| 5,863,520 | * | 1/1999 | Bichon et al. .............. 424/9.52 |
| 6,071,496 | * | 6/2000 | Stein et al. ................. 424/9.52 |

FOREIGN PATENT DOCUMENTS

| | | |
|---|---|---|
| 0 327 490 | 8/1989 | (EP) . |
| 93/25 241 | 12/1993 | (WO) . |
| 93/25 242 | 12/1993 | (WO) . |

\* cited by examiner

Primary Examiner—Gary E. Hollinden
(74) Attorney, Agent, or Firm—Michael J. Rafa; Felissa H. Cagan; Susan T. Evans

(57) ABSTRACT

The invention relates to gaseous microparticles for ultrasonic diagnosis, whose wall material is built up from block copolymers of polyesters of α-, β- or γ-hydroxycarboxylic acids with linear or star-shaped polyethylene glycols and optionally liquid crystals or whose wall material is built up from polyesters of α-, β- or γ-hydroxycarboxylic acids and liquid crystals, media that contain these particles for ultrasonic diagnosis, as well as a process for the production of the media and particles.

10 Claims, 1 Drawing Sheet

GASEOUS MICROPARTICLES FOR ULTRASONIC DIAGNOSIS AND PROCESS FOR THEIR PRODUCTION

This application is a 371 of PCT/EP96/01108 filed Mar. 14, 1996.

FIELD OF THE INVENTION

The invention relates to the object that is characterized in the claims, i.e., gaseous microparticles for ultrasonic diagnosis, whose wall material is built up from block copolymers of polyesters of α-, β- or γ-hydroxycarboxylic acids with linear or star-shaped polyethylene glycols and optionally liquid crystals or from polyesters of α-, β- or γ-hydroxycarboxylic acids and liquid crystals, media that contain these particles for ultrasonic diagnosis, as well as a process for the production of the media and particles.

BACKGROUND OF THE INVENTION

Ultrasonic diagnosis has been used very extensively in medicine because of the trouble-free, simple handling. Ultrasonic waves are reflected at interfaces of different types of tissues. The echo signals that are produced in this case are electronically enhanced and made visible.

The visualization of blood vessels and internal organs using ultrasound generally does not allow the visualization of the blood flow that is present in it. Liquids, especially blood, yield ultrasonic contrast only if density and compressibility differences exist compared to the surrounding area. In medical ultrasonic diagnosis, e.g., substances that contain gases or that produce gas are used as contrast media since the impedance difference between gas and surrounding blood is considerably greater than that of liquids or solids and blood [Levine, R. A., J. Am. Coll. Cardiol. 3 (1989) 28; Machi, I. J. CU 11 (1983) 3].

Roelandt et al. [Ultrasound Med. Biol. 8 (1982) 471–492] describe that cardial echo contrasts can be achieved by peripheral injections of solutions that contain fine gas bubbles. These gas bubbles are created in physiologically compatible solutions by, e.g., shaking, other stirring or by addition of carbon dioxide. They are not standardized with respect to number or size, however, and can be reproduced only inadequately. Also, they are generally not stabilized, so that their service life is short. Their average diameters in most cases exceed that of an erythrocyte, so that it is not possible for them to pass through the pulmonary capillaries with subsequent contrasting of organs such as left heart, liver, kidney or spleen. Moreover, they are not suitable for quantification since the ultrasonic echo that they produced consists of several processes that cannot be separated from one another, such as bubble production, coalescence and dissolution. Thus, it is not possible, e.g., with the aid of these ultrasonic contrast media to obtain information on transit times by measuring the history of the contrast in the myocardium. To this end, contrast media are needed whose scatter elements have sufficient stability.

EP 0 131 540 describes the stabilization of gas bubbles by sugar. This improves the reproducibility and homogeneity of the contrast effect, but these bubbles do not survive passing through the lungs.

EP 0 122 624 and 0 123 235 describe that the gas bubble-stabilizing effect of sugars, sugar alcohols, and salts is improved by the addition of surface-active substances. The passage through pulmonary capillaries and the possibility of visualizing the arterial femoral blood vessel and various organs such as the liver or spleen are provided for with these ultrasonic contrast media. In this case, however, the contrast effect is limited to the vascular lumen, since the bubbles are not absorbed by the tissue cells.

None of the ultrasonic contrast media described remains unaltered in the body for a prolonged period of time. Organ visualization with sufficient signal intensity by selective concentration after i.v. administration or quantification is not possible with these media.

Encapsulation of gases, such as, for example, air as ultrasonic contrast media is described in EP 0 224 934. The wall material that is used in this case consists of protein, especially human serum albumin with the known allergenic properties, which may also be accompanied by cytotoxic effects caused by denaturation.

Patent EP 0 327 490 describes gaseous microparticles for ultrasonic diagnosis based on biodegradable, synthetic materials. As biodegradable polymers, i.a., α-, β- or γ-hydroxycarboxylic acids are also disclosed. The diagnostic action of contrast medium preparations that are prepared therefrom is therefore not satisfactory in all cases.

A functional analysis is not possible with any of the ultrasonic contrast media described.

SUMMARY OF THE INVENTION

The object of this invention was therefore to find compounds and media prepared therefrom that overcome the drawbacks of the prior art.

This object is achieved by this invention.

DETAILED DESCRIPTION OF THE INVENTION

Figure 1:
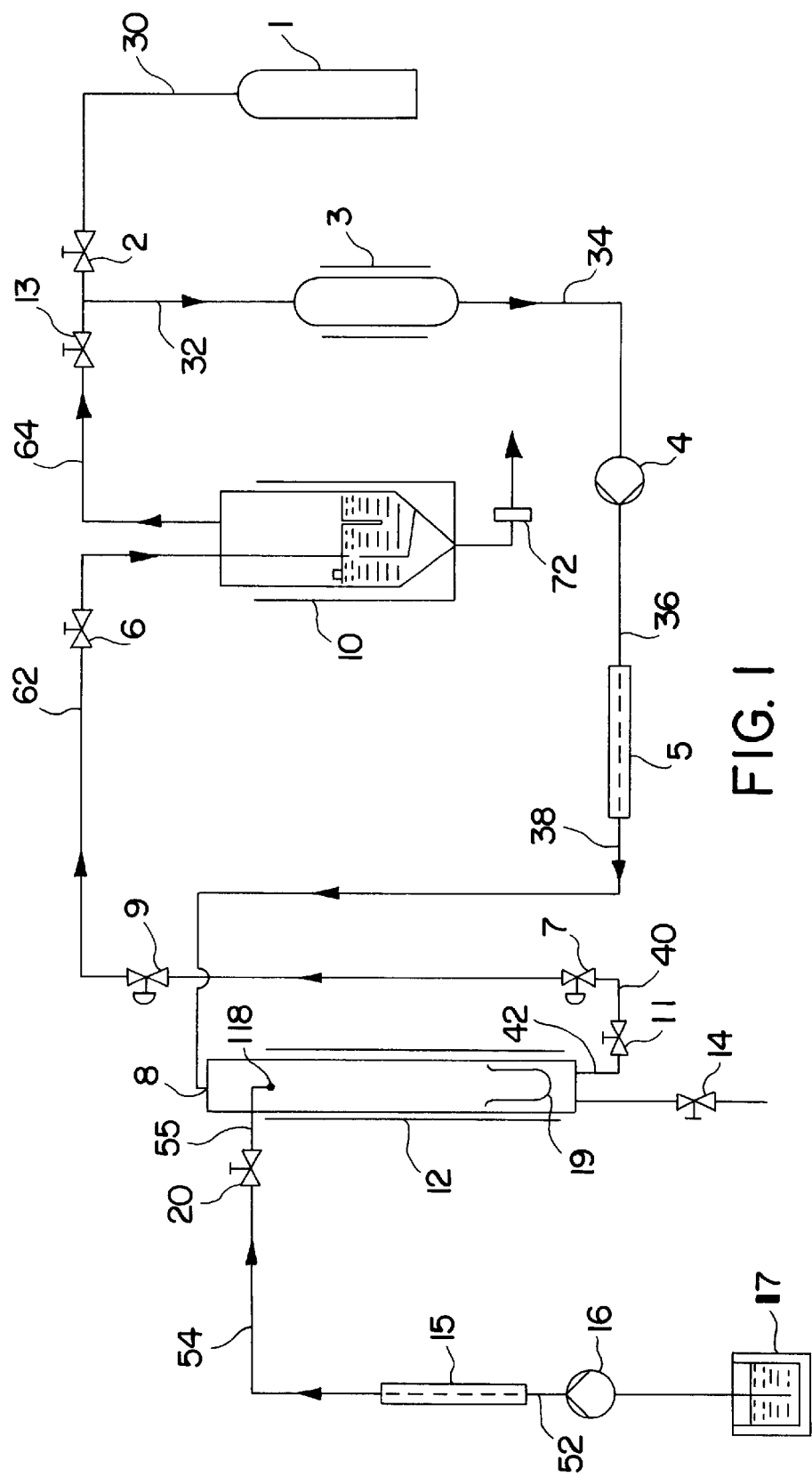
FIG. 1 depicts a schematic of the process used to produce the microparticles according to the invention.

It has been found that gaseous microparticles, whose wall material is built up from block copolymers of polyesters of α-, β- or γ-hydroxycarboxylic acids with linear or star-shaped polyethylene glycols and optionally liquid crystals or from polyesters of α-, β- or γ-hydroxycarboxylic acids and liquid crystals, are extremely well suited as ultrasonic contrast media.

As block copolymers that can be used according to the invention, there can be mentioned by way of example:

Glycolide-copolymers (PGA) with trimethylene carbonate (TMC) or lactide-copolymers (PLA) with trimethylene carbonate, tetramethylene glycolide, δ-valerolactone, ξ-caprolactone or block copolymers of polyesters of hydroxycarboxylic acids with linear or star-polyethylene glycol (PEG or S-PEG), such as, e.g., PLA/PEG AB-block copolymers, PLA/PEG/PLA ABA-block copolymers, S(3)-PEG-PLA block copolymers, S(4)-PEG-PLA block copolymers.

As liquid-crystalline components that are optionally contained in the polymeric wall material, there can be mentioned by way of example:

Polyoxyethylene trimethylolpropanedistearate (PTDS), polyoxyethylene glyceryl distearate (PGDS), polyoxyethylene distearate (PDS), polyoxyethylene stearyl ether stearate (PSES), polyoxyethylene lauryl ether stearate (PLES), monooxyethylene trimethylolpropane tristearate (MTTS*) as well as polyoxyethylene glyceryl tristearate (PGTS*) [the above-mentioned liquid-crystalline compounds are to be ordered from Nihon Emulsion Co. Ltd. (Tokyo)].

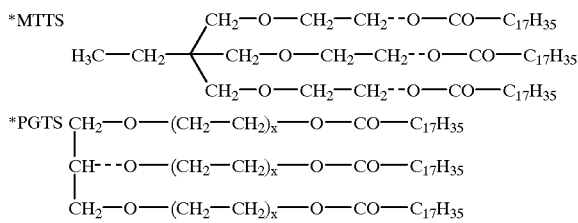

Microparticles according to the invention, in which the wall material contains liquid crystals, can be used preferably in functional analysis. Thus, the liquid crystals change their aggregate state as a function of temperature. At corresponding temperature, this leads to destruction of the particle shell, so that the enclosed gas can escape, which leads to disappearance of the ultrasonic echo. Phase transition temperatures are known for a considerable number of commercially available liquid crystals and can be taken from the manufacturer's data. Moreover, the retention time of the microparticles in the blood optionally can be controlled by the quantity that is added to the liquid-crystalline compound. The proportion of liquid crystals in the microparticles according to the invention is 0–30% (% by weight).

As gases that are contained in the particles, air, nitrogen, noble gases, dinitrogen oxide, carbon dioxide, halogenated hydrocarbons, saturated or unsaturated hydrocarbons, nitrogen dioxide and/or ammonia are used.

Another aspect of the invention relates to a process for the production of microparticles based on block copolymers of polyesters of α-, β- or γ-hydroxycarboxylic acids with linear or star-shaped polyethylene glycols and optionally liquid crystals as well as for the production of microparticles based on α-, β- or γ-hydroxycarboxylic acids and liquid crystals.

Such particles can be obtained by the respective polymer, optionally by adding the liquid-crystalline compound and optionally a surface-active substance in an organic solvent or solvent mixture, of which at least one solvent is readily water-miscible, being dissolved, then a liquid perfluoro compound or water being dispersed in this solution, and then this dispersion being dispersed in water that contains a surface-active substance with the aid of a stirring mechanism, whereby the solvent is removed by pumping in gas and applying a vacuum. In this case, particles that contain first water or the liquid perfluoro compound precipitate out. Then, the suspension that contains particles is mixed with a suitable pharmaceutically acceptable cryoprotector and freeze-dried, whereby the liquid that is contained in the particles largely escapes, and is replaced after the freeze-drying device is aerated with the desired gas (generally sterile air). Depending on the drying time, optionally a small amount of liquid (water or perfluoro compound) remains as vapor in the particles.

As organic solvents or solvent mixtures for the polymers, dichloromethane, acetone, ethyl acetate, methyl acetate, triacetin, triethyl citrate, ethyl lactate, isopropyl acetate, propyl formate, butyl formate, ethyl formate and/or methyl lactate are preferably used.

As a perfluoro compound, preferably perfluoropentane, perfluorohexane, perfluoro-1,3-dimethylcyclohexane, perfluorocyclohexene, perfluorodecalin or perfluoroether is used.

As a surface-active substance (surfactant), substances from the group of poloxamers or poloxamines, polyethylene glycol alkyl ethers, polysorbates, saccharose esters (Sisterna The Netherlands), saccharose esters [Ryoto sugar esters, (Tokyo)], gelatin, polyvinylpyrrolidone, fatty alcohol polyglycoside, Chaps (Serva), Chap (Calbiochem), Chapso (Calbiochem), decyl-β-D-glycopyranoside, decyl-β-D-maltopyranoside, dodecyl-β-D-maltopyranoside, sodium oleate, polyethylene glycol, polyvinyl alcohol or mixtures thereof are used.

An alternative process consists in the fact that the desired polymer(s) and optionally an amino acid in at least one organic solvent are dissolved, this solution is sprayed via a nozzle into a column, which is filled with a supercritical gas or through which the latter flows, whereby the solvent is taken up by supercritical gas.

Preferably, in this process variant, an amino acid is provided instead of the surfactant in the dissolved polymers (polyesters) that are used in each case. As amino acids, preferably L-lysine, L-phenylalanine, L-tryptophan as well as D,L-phenylalanine are used.

The addition of a perfluoro compound is not necessary in this case.

As solvents or solvent mixtures, the above-mentioned solvents are suitable.

As supercritical gases, dinitrogen oxide, carbon dioxide, halogenated hydrocarbons, saturated or unsaturated hydrocarbons, nitrogen dioxide and/or ammonia are used, whereby carbon dioxide is preferred. The supercritical gases can optionally contain up to 10% additives such as, e.g., lower alcohols, such as, e.g., ethanols, esters or gases, such as, e.g., nitrogen.

The size of the resulting particles can be controlled by type, size and shape of the injection nozzle, working pressure and temperature in the column. A particle size as is necessary for an intravenously administered ultrasonic contrast medium (<10 μm) can be obtained by using a nozzle with a nozzle diameter of 0.5 mm and a spraying angle of 10° at a working pressure of between 90 and 100 bar, preferably 94–96 bar and a temperature of 36° C.

Another aspect of the invention relates to contrast media for ultrasonic diagnosis that contain the gaseous microparticles according to the invention.

These media can be produced by the dried microparticles being resuspended in a pharmaceutically acceptable suspension medium.

As pharmaceutically acceptable suspension media, for example, water p.i., aqueous solutions of one or more inorganic salts, such as physiological electrolyte solutions and buffer solutions, such as, e.g., Tyrode's solution, aqueous solutions of mono- or disaccharides such as glucose or lactose, sugar alcohols such as mannitol, which optionally in addition have a surface-active substance, e.g., from the group of polysorbates or polysaccharides, polyvinylpyrrolidone, polyethylene glycol, saccharose mono- and diesters or substances from the group of poloxamers or poloxamines or mixtures thereof and/or a physiologically compatible multivalent alcohol such as glycerine are suitable. Preferred is, however, water that is suitable for injection purposes.

To increase the reliability of the administration, the suspension can be filtered immediately before injection.

The microparticles according to the invention that are based on block copolymers of polyesters of α-, β- or γ-hydroxycarboxylic acids with linear or star-shaped polyethylene glycols and optionally liquid crystals or based on polyesters of α-, β- or γ-hydroxycarboxylic acids and liquid crystals, as well as contrast media that are prepared from them, meet all requirements that are set on a modern ultrasonic contrast medium. The particles that are contained in the media are distinguished by the following advantages:

They are quickly degraded in vivo,
degradation products are toxicologically harmless,
they circulate for a sufficiently long period in the blood circulation,
they can be used in all modes of ultrasonic diagnosis, especially also in modes in which nonlinear effects can be used,
they are well-tolerated,
they show a uniform, controllable size distribution,
they are easy to produce,
they are sufficiently stable to survive passing through the lungs and thus are also suitable for contrasting the left heart and
they are taken up by the reticuloendothelial system and thus are also suitable for contrasting the liver and spleen.

The particles and contrast medium preparations that are produced therefrom are, moreover, well-tolerated without having an allergenic potential and do not agglomerate in aqueous medium. In addition, the microparticles according to the invention, whose particle shell contains a liquid-crystalline compound, are suitable for functional analysis.

Below is a summary of the abbreviations that are used in the application. Here:

PLA means polylactide
PGA means polyglycolide
TMC means trimethylene carbonate
S means star
S(x) means a star with x-fold branches, whereby in a 3-x branching the branching point is a nitrogen atom, and in a 4-x branching, the branching point is an ammonium ($N^+$) ion or a carbon atom,
AB or ABA refers to the sequence of the monomer structural elements.

The examples below are used for a more detailed explanation of the object of the invention, without intending that it be limited to these examples.

EXAMPLE 1

3 g of diblock copolymer of polylactide and polyethylene glycol (PLA 9600/PEG 2100) that can be produced as described by K. J. Zhu et al. [Journal of Applied Polymer Science Vol. 39 (1990) 1–9 or Journal of Polymer Science (Part A: Polymer Letters) Vol. 24 (1986) 331–337], D. Shiaw-Guang Hu et al. [Polymer Bulletin 30, (1993) 669–676] or X. M. Deng et al. [Journal of Polymer Science (Part C: Polymer Letters) Vol. 28 (1990) 411–416] is dissolved in 40 ml of methylene chloride/acetone (volume proportion 50:50). 10 ml of perfluoropentane is dispersed for 2 minutes (10,000 rpm) in the polymer solution using Ultraturrax. The emulsion that is produced (O/O) is dispersed for 30 minutes (1,000 rpm) in 400 ml of a 1% gelatin solution, which is temperature-equalized at 0° C., using a mechanical stirring mechanism (Dispermat-FT, VMA-Getzmann GmbH). The emulsion (O/O/W) is moved into a 2 l three-necked flask that is equipped with a stirring mechanism (300 rpm), and the solvent is removed for 3 hours at 20° C. by pumping in $N_2$ and for 3 hours at 25° C. by vacuum. Then, the suspension is mixed with a cryoprotector and freeze-dried.

The lyophilizate that is resuspended with water contains ultrasound-active microparticles with a diameter of 0.1 to 4 µm. The determination of the particle diameter is done with an LS-130 from the Coulter Electronics GmbH company.

EXAMPLE 2

The procedure is as in Example 1, whereby 1% gelatin solution is replaced by 0.2% gelatin solution and the diblock copolymer is replaced by triblock copolymers of polylactide and polyethylene glycol (ABA). This block polymer can be obtained as described in H. R. Kricheldorf et al. [Makromol. Chem. 194 (1993) 463], Li Youxin et al. [Journal of Controlled Release, 27 (1993) 247–257].

The lyophilizate that is resuspended with water contains ultrasound-active microparticles with a diameter of 0.1 to 4 µm.

EXAMPLE 3

The procedure is as in Example 1, whereby 1% gelatin solution was replaced by 0.1% gelatin solution and the diblock copolymer was replaced by star-polyethylene glycol-polylactide copolymer (S(3) PEG-PLA). This polymer can be obtained as described in K. J. Zhu [Journal of Polymer Science (Part A: Polymer Chemistry) Vol. 27 (1989) 2151–2159].

The lyophilizate that is resuspended with water contains ultrasound-active microparticles with a diameter of 0.1 to 2 µm.

EXAMPLE 4

The procedure is as in Example 1, whereby the diblock copolymer is replaced by a triblock copolymer PLA-S(3)-PEG-PLA. This polymer can be produced as described by K. J. Zhu [Journal of Polymer Science: Part A Polymer Chemistry, Vol. 27 (1989) 2151–2159].

The lyophilizate that is resuspended with water contains ultrasound-active microparticles with a diameter of 0.1 to 5 µm.

EXAMPLE 5

The procedure is as in Example 1, whereby the diblock copolymer was replaced by star-polyethylene glycol-polylactide (S(4)-PEG-PLA). This polymer can be produced as described by K. J. Zhu [Journal of Polymer Science: Part A Polymer Chemistry, Vol. 27 (1989) 2151–2159].

The lyophilizate that is resuspended with water contains -ultrasound-active microparticles with a diameter of 0.1 to 2 µm.

EXAMPLE 6

The procedure is as in Example 1, whereby the diblock copolymer is replaced by a triblock copolymer (PLA-S(4)-PEG-PLA. This polymer can be produced as described by K. J. Zhu [Journal of Polymer Science: Part A Polymer Chemistry, Vol. 27 (1989) 2151–2159].

The lyophilizate that is resuspended with water contains ultrasound-active microparticles with a diameter of 0.1 to 4 µm.

EXAMPLE 7

The procedure is as in Example 1, whereby in the methylene chloride/acetone solution, in addition to the diblock copolymer, 300 mg of liquid crystal MTTS [Nihon Emulsion Co. Ltd. (Tokyo)] is also dissolved.

The lyophilizate that is resuspended with water contains ultrasound-active microparticles with a diameter of 0.3 to 7 µm.

EXAMPLE 8

The procedure is as in Example 1, whereby in addition to the diblock copolymer, 300 mg of liquid crystal PGTS [Nihon Emulsion Co. Ltd. (Tokyo)] is also dissolved in the methylene chloride/acetone solution. The lyophilizate that is resuspended with water contains ultrasound-active microparticles with a diameter of 0.3 to 7 μm.

EXAMPLE 9

0.375 g of L-lysine (Aldrich) is dissolved in 25 ml of glacial acetic acid (Merck) and mixed with 2.5 g (PLA-PEG) (Böhringer Ingelheim), dissolved in 75 ml of dichloromethane (Merck). The combined solutions are further treated in an apparatus as pictured in FIG. 1.

The combined solutions are first added to a tank (17), and the unit filled with gas via valve (2) and line (30) from a storage bottle. Using a reciprocating pump (16), the solution is fed to nozzle (118) from tank (17) after flowing through line (52) to a heat exchanger (15), a line (54), a valve (20) and finally line (55). At a pressure of 94–96 bar, the solution that contains the copolymer is sprayed into column (12) by a conventional one-component nozzle (118) [Schlick 121 V type], whereby simultaneously $CO_2$ in a supercritical state is directed through the column with 90 bar/36° C. and a throughput of 8.9 kg/h in parallel flow, via intake (8). The nozzle has a diameter of 0.5 mm, and the spraying angle is 10°.

Corresponding to the high affinity of the supercritical $CO_2$ for the solvent, solvent is removed from the primarily formed droplets. Spherical solid polymer particles remain.

The additional steps are used basically to purify and recycle the solvent-charged $CO_2$, but no longer have anything to do with the production of particles. The working-up of the $CO_2$ can be done as follows. The gas that is charged with solvent flows out the end of the column through lines (42) and (40), controlled by 2 magnet valves (7 and 9), and is expanded to 60 bar. The valves are switched in such a way that the quantity of liquid gas that flows into the column per unit of time can flow in while maintaining the working pressure of the column. The $CO_2$, which is cooled by expansion to 60 bar and charged with solvent, is directed by line (62) into separator (10) that is temperature-equalized to 21° C., where the solvent mixture separates into $CO_2$ because of the strongly reduced solubilities under these conditions. The $CO_2$ from which the solvent mixture is removed is brought back into the supercritical state (90 bar, 36° C.) using lines (64 and 32) by raising the pressure and temperature (3 and 4), and to further dry the particles that are produced it is again fed to the column via line (34), liquid gas pump (4), line (36), heat exchanger (5), line (38) via intake (8).

The removal of the solvent mixture that is separated in separator (10) is done after separator (10) is separated from the circuit by valves (6) and (13) and after depressurization to atmospheric pressure is done via valve (72).

After the entire quantity of dissolved polymer contained in the reservoir has been sprayed (time period, depending on pressure, 20 to 50 minutes), $CO_2$ is run through the column until solvent radicals can no longer be recovered in separator (10).

After the drying process has ended, the $CO_2$ flow to the column is shut off, the column above valves (11) and (14) is depressurized to atmospheric pressure, and the particles are removed at lower column end (19).

Ultrasound-active, gaseous microparticles with a diameter of 1–10 μm are obtained.

EXAMPLES 10–16

The production of further microparticles is done analogously to Example 9. The polymers that are used in each case as well as additional data are summarized in Table 1.

In all cases, ultrasound-active, gaseous microparticles are obtained. The particles that are obtained are sterile and free of solvent residue, polymerization catalysts or initiator molecules. They have a uniform particle size distribution of 1 to 10 μm.

The polymers are dissolved in each case in 75 ml of dichloromethane (Merck) and 25 ml of glacial acetic acid, and the respective quantity of amino acid is added. D,L-Phenylalanine is suitably to be dissolved in advance in up to 50 ml of ethanol (Merck).

TABLE 1

| Test Number | Polymer | Weighed Portion of Polymer [g] | Amino Acid | Weighed Portion of Amino Acid [g] |
|---|---|---|---|---|
| 10 | Poly-(D,L-lactide-co-trimethyl-carbonate) | 2.0 | L-lysine | 0.3 |
| 11 | Poly-(D,L-lactide-co-glycolide)-PEG-block polymer | 1.0 | L-phenyl-alanine | 0.15 |
| 12 | Poly-PLA-PEG-PLA-block polymer | 2.0 | D,L-phenyl-alanine | 0.3 |
| 13 | S(3)-PEG-PLA-star block copolymer | 2.2 | L-tryptophan | 0.35 |
| 14 | S(4)-PEG-PLA-star block copolymer | 3.0 | L-lysine | 0.25 |
| 15 | PLA-S(4)-PEG-PLA-star block copolymer | 2.0 | L-lysine | 0.2 |
| 16 | PLA-S(3)-PEG-PLA-star block copolymer | 2.0 | L-lysine | 0.15 |

What is claimed is:

1. Gaseous microparticles for use in ultrasonic diagnosis, characterized in that the wall material of the particles is built up from block copolymers of polyesters of α-, β-, or γ-hydroxycarboxylic acids with linear or star-shaped polyethylene glycols and liquid crystals or from polyesters of α-, β-, or γ-hydroxycarboxylic acids and liquid crystals.

2. Gaseous microparticles according to claim 1 wherein the wall material is built up from glycolide-copolymers with trimethylene carbonate or lactide-copolymers with trimethylene carbonate tetramethylene glycolide, δ-valerolactone or ξ-caprolactone or block copolymers of polyesters of hydroxycarboxylic acids with linear- or star-polyethylene glycol, PLA/PEG AB-block copolymers, PLA/PEG/PLA ABA block copolymers, s(3)-PEG-PLA block copolymers or S(4)-PEG-PLA block copolymers.

3. Gaseous microparticles according to claim 1 wherein the liquid-crystalline compound is selected from the group consisting of polyoxyethylene trimethylolpropanedistearte, polyoxyethylene glyceryl distearte, polyoxyethylene distearte, polyoxyethylene stearyl ether stearate, polyoxyethylene lauryl other stearate, monooxyethylene trimethylolpropane tristearate or polyoxyethylene glyceryl tristearate.

4. Gaseous microparticles according to claim 3, wherein the proportion of liquid-containing compound is up to 30% by weight.

5. Gaseous microparticles according to claim 1 further comprising a gas selected from the group consisting of air, nitrogen, noble gases, dinitrogen oxide, carbon dioxide, halogenated hydrocarbons, saturated or unsaturated hydrocarbons, nitrogen dioxide and/or ammonia.

6. Process for the production of gaseous microparticles for ultrasonic diagnosis, whose wall material is built up from block copolymers of polyesters of α, β-, or γ-hydroxycarboxylic acids with linear or star-shaped polyethylene glycols and liquid crystals or from polyesters of α-, β-, or γ-hydroxycarboxylic acids and liquid crystals, wherein the desired polymer, and optionally a surface-active substance are dissolved in an organic solvent or solvent mixture, of which at least one solvent is readily water-miscible, then a gaseous perfluoro compound or water is dispersed in this solution at body temperature and them this dispersion is dispersed in water that contains a surface-active substance using a stirring mechanism, whereby the solvent is removed by pumping in gas and applying a vacuum, and finally the suspension that is thus obtained is mixed with a suitable pharmaceutically acceptable cryoprotector and freeze-dried.

7. Process according to claim 6, wherein the surface-active substance is selected from the group consisting of poloxamers, poloxamines, polyethylene glycol alkyl ethers, polysorbates, saccharose esters, gelatin, polyvinylpyrrolidone, fatty alcohol polyglycoside, Chaps, Chap, Chapso, decyl-β-D-glycopyranoside, decyl-β-D-maltopyranoside, dodecyl-β-D-maltopyranoside, sodium oleate, polyethylene glycol, polyvinyl alcohol or mixtures thereof.

8. Process according to claim 6 wherein the perfluoro compound is selected from the group consisting of perfluoropentane, perfluorohexane, perfluoro-1,3-dimethylcyclohexane, perfluorocyclohexane, perfluorodecalin and perfluoroether.

9. Process according to claim 6 wherein the organic solvent for the polymer is selected from the group consisting of dichloromethane, acetone, ethyl acetate, methyl acetate, triacetin, triethyl citrate, ethyl lactate, isopropyl acetate, propyl formate, butyl formate, ethyl formate, and methyl lactate.

10. Process for the production of contrast media for ultrasonic diagnosis, wherein microparticles according to claim 1 are suspended in a pharmaceutically compatible suspension medium.

* * * * *